United States Patent [19]
Kusleika

[11] Patent Number: 5,836,912
[45] Date of Patent: Nov. 17, 1998

[54] CATHETER HAVING NONLINEAR FLOW PORTION

[75] Inventor: Richard S. Kusleika, Eden Prairie, Minn.

[73] Assignee: Schneider (USA) Inc., Plymouth, Minn.

[21] Appl. No.: 734,350

[22] Filed: Oct. 21, 1996

[51] Int. Cl.$^6$ .................................................. A61M 29/00
[52] U.S. Cl. ............................................. 604/96; 604/280
[58] Field of Search .......................... 604/96–103, 264, 604/280; 606/192, 194

[56] References Cited

U.S. PATENT DOCUMENTS

| | | | |
|---|---|---|---|
| 4,335,723 | 6/1982 | Patel | 128/349 B |
| 4,563,180 | 1/1986 | Jervis et al. | 604/280 |
| 4,596,563 | 6/1986 | Pande | 604/264 |
| 4,646,742 | 3/1987 | Packard et al. | 128/344 |
| 4,762,129 | 8/1988 | Bonzel | 128/344 |
| 4,906,241 | 3/1990 | Noddin et al. | 606/194 |
| 4,921,483 | 5/1990 | Wijay et al. | 604/96 |
| 4,976,690 | 12/1990 | Solar et al. | 604/96 |
| 5,066,282 | 11/1991 | Wijay et al. | 604/152 |
| 5,108,369 | 4/1992 | Ganguly et al. | 604/96 |
| 5,156,595 | 10/1992 | Adams | 604/96 |
| 5,158,540 | 10/1992 | Wijay et al. | 604/43 |
| 5,244,619 | 9/1993 | Burnham | 264/173 |
| 5,284,473 | 2/1994 | Calabria | 604/53 |
| 5,295,961 | 3/1994 | Niederhauser et al. | 604/96 |
| 5,342,297 | 8/1994 | Jang | 604/53 |
| 5,403,292 | 4/1995 | Ju | 604/282 |
| 5,425,711 | 6/1995 | Ressemann et al. | 604/96 |
| 5,425,712 | 6/1995 | Goodin | 604/96 |
| 5,489,264 | 2/1996 | Salo | 604/28 |
| 5,496,292 | 3/1996 | Burnham | 604/282 |

FOREIGN PATENT DOCUMENTS

| | | |
|---|---|---|
| 0597465A1 | 5/1994 | European Pat. Off. . |
| 970645 | 9/1964 | United Kingdom . |
| 9108014 | 6/1991 | WIPO . |
| 9109640 | 7/1991 | WIPO . |

*Primary Examiner*—Wynn Wood Coggins
*Assistant Examiner*—Cris L. Rodriguez
*Attorney, Agent, or Firm*—Peter C. Richardson; Lawrence C. Akers; Philip C. Strassburger

[57] ABSTRACT

An improved catheter having at least one lumen with a nonlinear inflation lumen flow portion that may be used with a balloon or in a guide catheter. Additionally disclosed is a catheter assembly having a nonlinear flow portion for contrast media delivery. The nonlinear flow portions facilitate hydraulic and mechanical characteristics relating to deflation of a balloon, the flow rate of fluid, contrast media or the like, and relative performance.

23 Claims, 8 Drawing Sheets

| BALLOON CATHETER | INFLATE TIME | DEFLATE TIME |
|---|---|---|
| CONSTANT INSIDE DIAMETER 2.9F SHAFT | 4.3 SEC. | 33.9 SEC. |
| NONLINEAR TAPERED INSIDE DIAMETER 3.5F/2.9F TAPER | 3.1 SEC. | 19.2 SEC |
| NONLINEAR TAPERED INSIDE DIAMETER 4.0F/2.9F TAPER | 2.4 SEC. | 14.2 SEC |

| BALLOON CATHETER | FLOW RATE |
|---|---|
| CONSTANT OUTSIDE DIAMETER 3.1F SHAFT | 458 cc/min |
| NONLINEAR TAPERED OUTSIDE DIAMETER 3.5F/2.9F TAPER | 517 cc/min |
| NONLINEAR TAPERED INSIDE DIAMETER 4.0F/2.9F TAPER | 462 cc/min |

CATHETER HAVING NONLINEAR FLOW PORTION

BACKGROUND OF THE INVENTION

This invention relates generally to catheters, and more particularly to catheters, balloon catheters, or balloon and guide catheter assemblies having a nonlinear flow portion.

Catheters are used in percutaneous transluminal coronary angioplasty and other medical procedures to administer medical treatment. For example, medical personnel will often use a balloon catheter to open a stenosis in an artery. This medical procedure often requires various sized balloon catheters to be used within a guide catheter. The balloon catheter and guide catheter sizes are generally dependent on the medical procedure and access to the treatment area.

During angioplasty, medical personnel generally prefer rapid balloon deflation and desire a relatively high flow rate of contrast media or the like through the balloon and guide catheter assembly in order for visual identification of the treatment area and for general efficient medical treatment. The need for generally rapid deflation of the balloon catheter and relatively high fluid flow rate through the balloon and guide catheter assembly has become more important with advances in micro-surgery, neuro-surgery, and conventional angioplasty procedures. Overall, there is a need for smaller catheters, balloon catheters, guide catheters, and balloon and guide catheter assemblies having superior hydraulic and mechanical performance.

Balloon and guide catheters require superior mechanical characteristics because they are often pushed a significant distance from the body access site. For example, during angioplasty, a catheter or balloon catheter may be disposed in a guide catheter lumen and the distal end may be pushed beyond the distal end of the guide catheter, through numerous tortuous arteries, to reach the treatment area. Manipulation of the catheter generally requires: the proximal portion of the balloon catheter to be relatively stiff; the distal portion of the balloon catheter to be relatively flexible; and the catheter shaft to have a relatively small profile.

Once the balloon catheter is disposed in the guide catheter, contrast media, blood product, medicant, therapeutic, or other products may be injected into the arteries.

Various types of balloon and guide catheters are commercially available.

SUMMARY OF THE INVENTION

The object of the invention is to provide a catheter, balloon catheter, or balloon and guide catheter assembly with generally improved hydraulic and mechanical performance using a novel nonlinear flow portion in the catheters.

In the catheter or balloon catheter, a nonlinear decreasing inflation lumen flow cross-sectional area distally along at least a portion of the longitudinal axis advantageously provides: a relatively greater diameter proximal portion shaft that allows relatively greater proximal pushability and stiffness without inhibiting the flow rate through a balloon and guide catheter assembly; a relatively smaller distal shaft diameter that allows relatively greater flexibility; and relatively faster balloon deflation.

In the balloon and guide catheter assembly, a nonlinear increasing flow cross-sectional area distally along at least a portion of the longitudinal axis advantageously relatively improves the fluid flow rate. The flow cross-sectional area is formed between the outside surface of the balloon catheter and the inside surface of the guide catheter and extends along at least a portion of the length of the coextensive shafts to form a flow portion.

Other therapeutic or diagnostic devices such as a stent delivery catheter, irradiating catheter, ultrasound imaging catheter, or atherectomy device may be used in conjunction with the present invention.

In sum, the invention relates to an intravascular catheter including an elongated tube having a proximal portion and a distal portion. The elongated tube has an outside diameter and at least one lumen with a longitudinal length and adapted to form a flow cross-sectional area. The flow cross-sectional area changes nonlinearly in at least a portion of the at least one lumen and the at least one lumen communicates with a balloon. The outside diameter may decrease nonlinearly on at least a portion of the elongated tube. The elongated tube may have wall of a substantial uniform thickness. The flow cross-sectional area may decrease at least 50 % within about the first 25 % of the lumen longitudinal length measured from the proximal end. An angle may formed by an imaginary line drawn between a proximal most nonlinear flow portion outside surface point of the proximal portion and a distal most nonlinear flow portion outside surface point of the distal portion with the catheter longitudinal axis of between about 1 degree and about 0.01 degree. The elongated tube may be made from one or more segments The outside diameter at the proximal portion may be greater than or equal to the outside diameter at the distal portion. The flow cross-sectional area may decreases nonlinearly distally. The flow cross-sectional area may decrease nonlinearly distally until between about 10% and about 60% of the lumen longitudinal length measured from the proximal end. The flow cross-sectional area may change at a nonuniform or nonconstant rate per unit of axial length. The elongated tube may be at least partially inserted into a second elongated tube. The flow cross-sectional area may decrease at least 20% distally along the longitudinal length. The lumen may have at least one portion that is substantially constant. The flow cross-sectional area may have circular, annular, oblong, or irregular shapes.

The invention also relates to an intravascular catheter assembly including a first elongated tube with at least one lumen, a first flow cross-sectional area, an outside diameter, a proximal end, a distal portion, and an outside surface. The outside diameter changes nonlinearly on at least one portion of the first elongated tube. A second elongated tube has a longitudinal length, at least one lumen and an inside surface. The first elongated tube is disposed at least partially in the second elongated tube lumen forming a second flow cross-sectional area between the first elongated tube outside surface and the second elongated tube inside surface. The first elongated tube has at least one lumen communicating with a balloon. The second flow cross-sectional area may increase nonlinearly distally. The second elongated tube may have a substantially constant inside diameter. The second flow cross-sectional area nonlinearly distally until between about 10% and about 60% of the longitudinal length measured from the proximal end. The first flow cross-sectional area may decrease nonlinearly in at least a portion distally. The second flow cross-sectional area may increase nonlinearly in at least a portion distally. The second flow cross-sectional area may increase at least 20% distally along the longitudinal length. The at least one portion of the first or second flow cross-sectional area may be substantially constant. The first or second flow cross-sectional area may change at a nonuniform or nonconstant rate per unit of change in axial length.

The invention also relates to a kit for a medical procedure including a guide catheter, a balloon catheter having a first nonlinear flow portion. The balloon catheter may be adapted to be at least partially disposed within the guide catheter to form a second nonlinear flow portion.

The invention also relates to an intravascular catheter including an elongated tube having a proximal portion and a distal portion. The elongated tube has an outside diameter and at least one lumen. The at least one lumen is adapted to form a flow cross-sectional area that decreases at a nonuniform rate per unit of change in axial length from the proximal portion to at least the distal portion. The at least one lumen communicates with a balloon.

The invention also relates to an intravascular catheter assembly including a first elongated tube having at least one lumen forming a first flow portion and a first outside diameter at the proximal portion, a second outside diameter at the distal portion, and an outside surface. The first outside diameter decreases nonlinearly along the longitudinal axis from the first outside diameter to the second outside diameter. A second elongated tube has at least one lumen and an inside surface. The first elongated tube is disposed at least partially in the second elongated tube forming a second flow portion between the first elongated tube outside surface and the second elongated tube inside surface.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

DETAILED DESCRIPTION OF THE INVENTION

Figure 1:
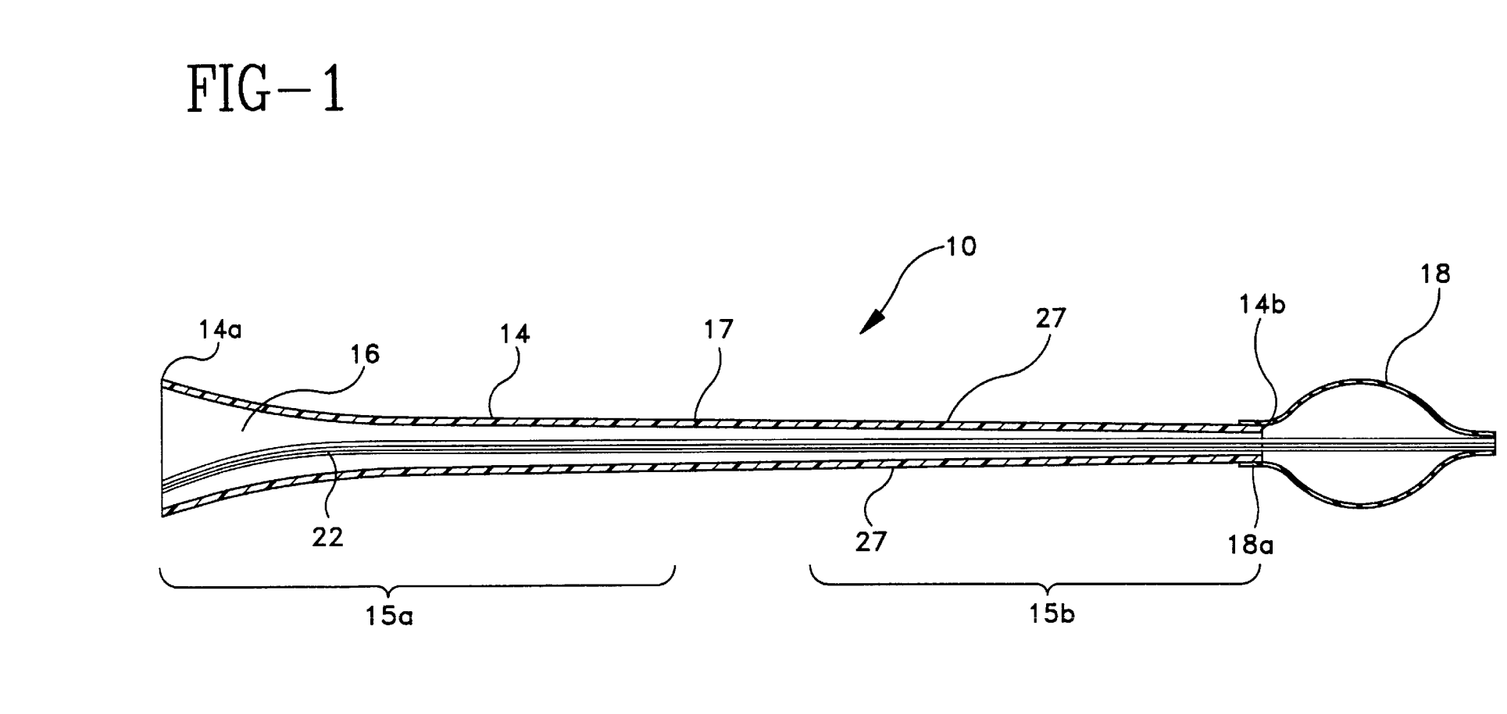
FIG. 1 is a sectional view of a balloon catheter embodying the present invention.
Figure 2:
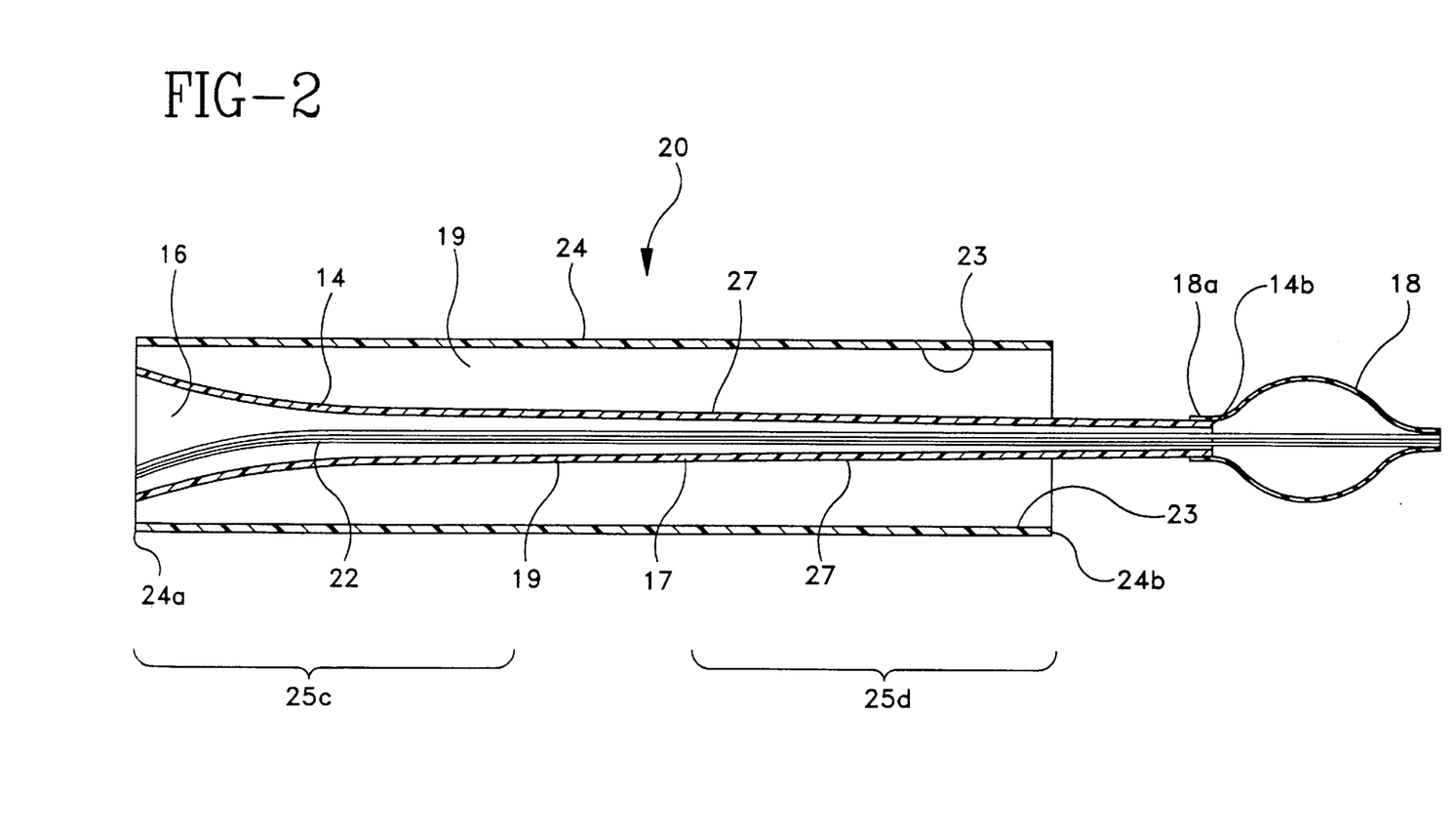
FIG. 2 is a sectional view of a balloon and guide catheter assembly embodying the present invention.
Figure 7A:
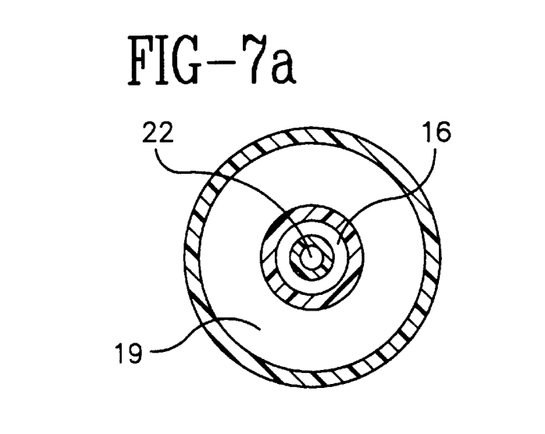
FIGS. 7a–e are various embodiments of lumen cross-sections.
Figure 7B:
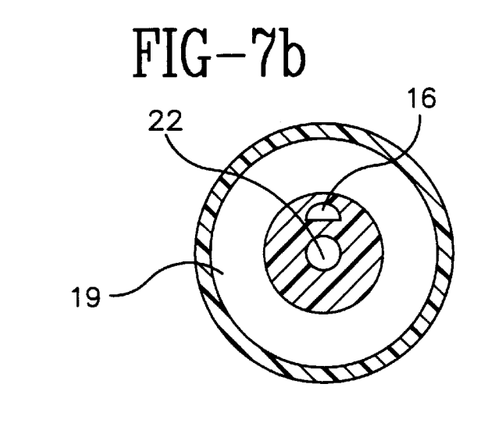
Figure 7C:
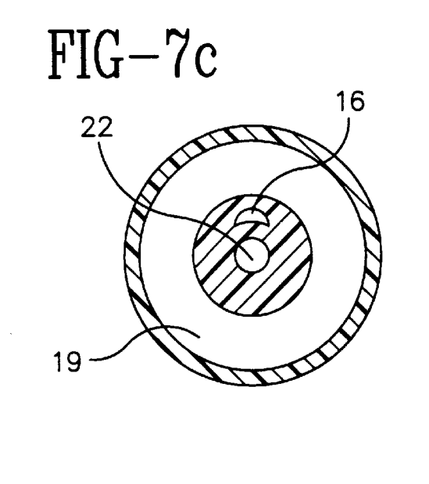
Figure 7D:
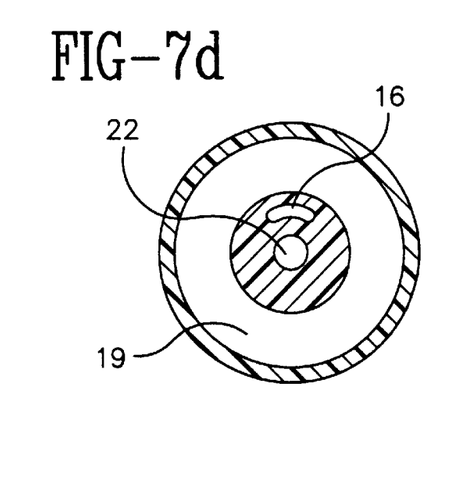
Figure 7E:
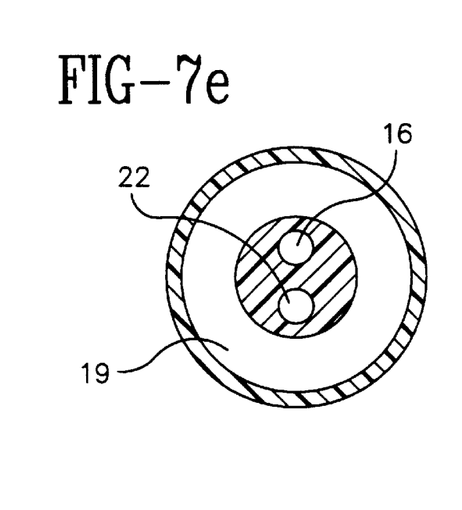

Reference is made to FIG. 1 and FIG. 2 of the drawings which illustrate preferred embodiments of the balloon catheter 10 according to the present invention showing an elongated tube 14 having a wall of substantial uniform thickness connecting and communicating with a balloon 18. The elongated tube 14 has a nonlinear inflation lumen flow portion 16 extending from the proximal end 14a through the body of the elongated tube 14 to a distal end 14b. In the balloon catheter 10, or the balloon and guide catheter assembly 20 illustrated in FIG. 2, the inflation lumen flow portion 16 or flow portion 19 may comprise a variety of flow cross-sectional area shapes, such as circular, oblong, irregular, annular, or a combination of shapes, along each respective axis or coextensive axis. For example, an annular cross-section 16 is shown in FIG. 7a. Additional circular related and oblong related cross-sections are shown in FIGS. 7b–e and may be incorporated in other embodiments of the invention. Other irregular shapes or a combination of shapes are also possible. The inflation lumen flow portion 16 of balloon catheter 10 or balloon and guide catheter assembly 20 generally has a profile that decreases nonlinearly distally along the length of the catheter.

In another embodiment, the balloon catheter 10 may have a flow cross-sectional area in the proximal portion 15a of flow portion 16 that nonlinearly decreases distally to a smaller flow cross-sectional area at the distal portion 15b. In still another embodiment, the balloon catheter 10 may have an outside diameter at the proximal portion 15a that nonlinearly decreases along the longitudinal axis to a smaller outside diameter at the distal portion 15b. In another embodiment, the elongated tube 14 may be partially inserted in the elongated tube 24.

Figure 6:
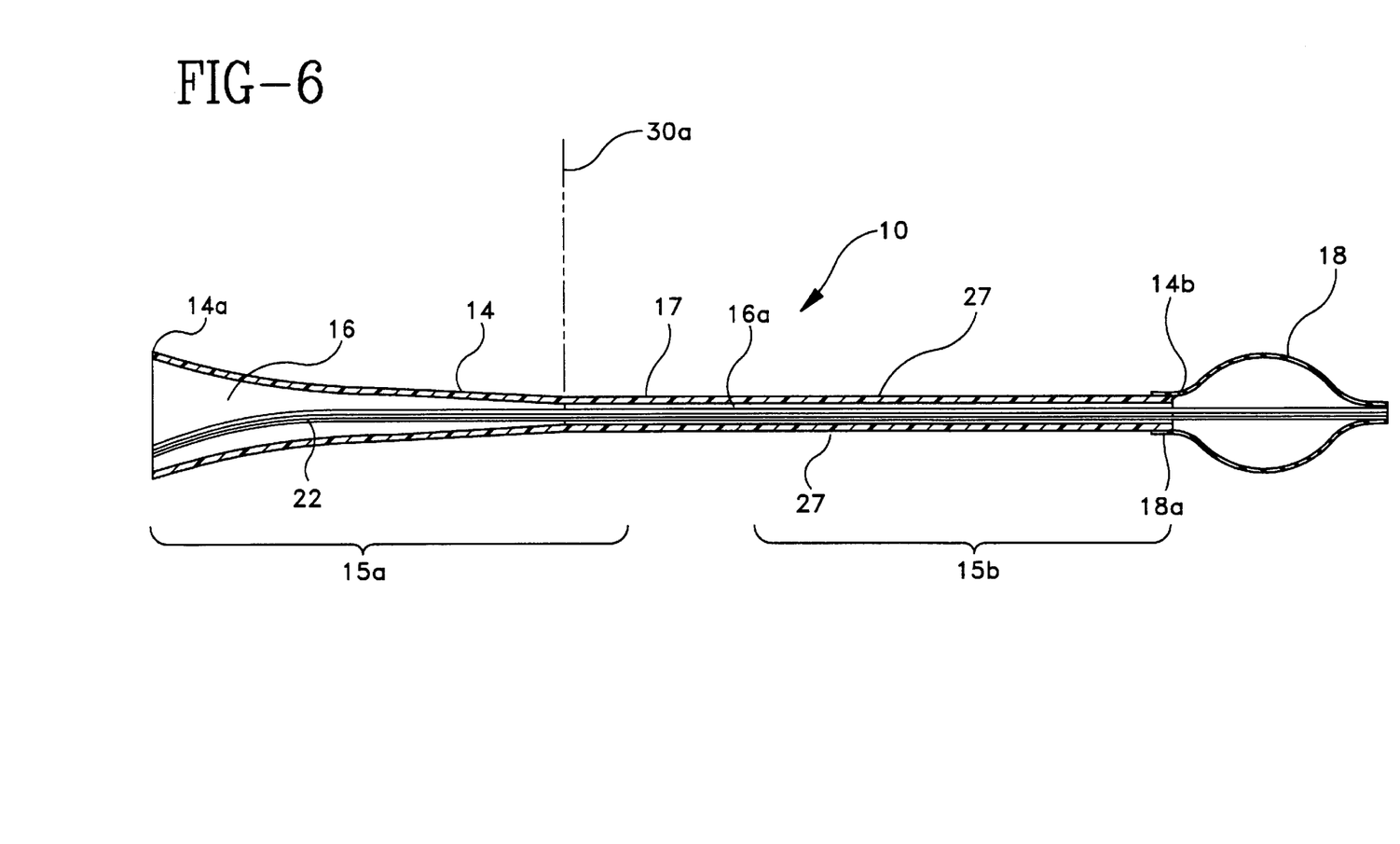
FIG. 6 is a sectional view of an embodiment of a balloon catheter.
Figure 8:
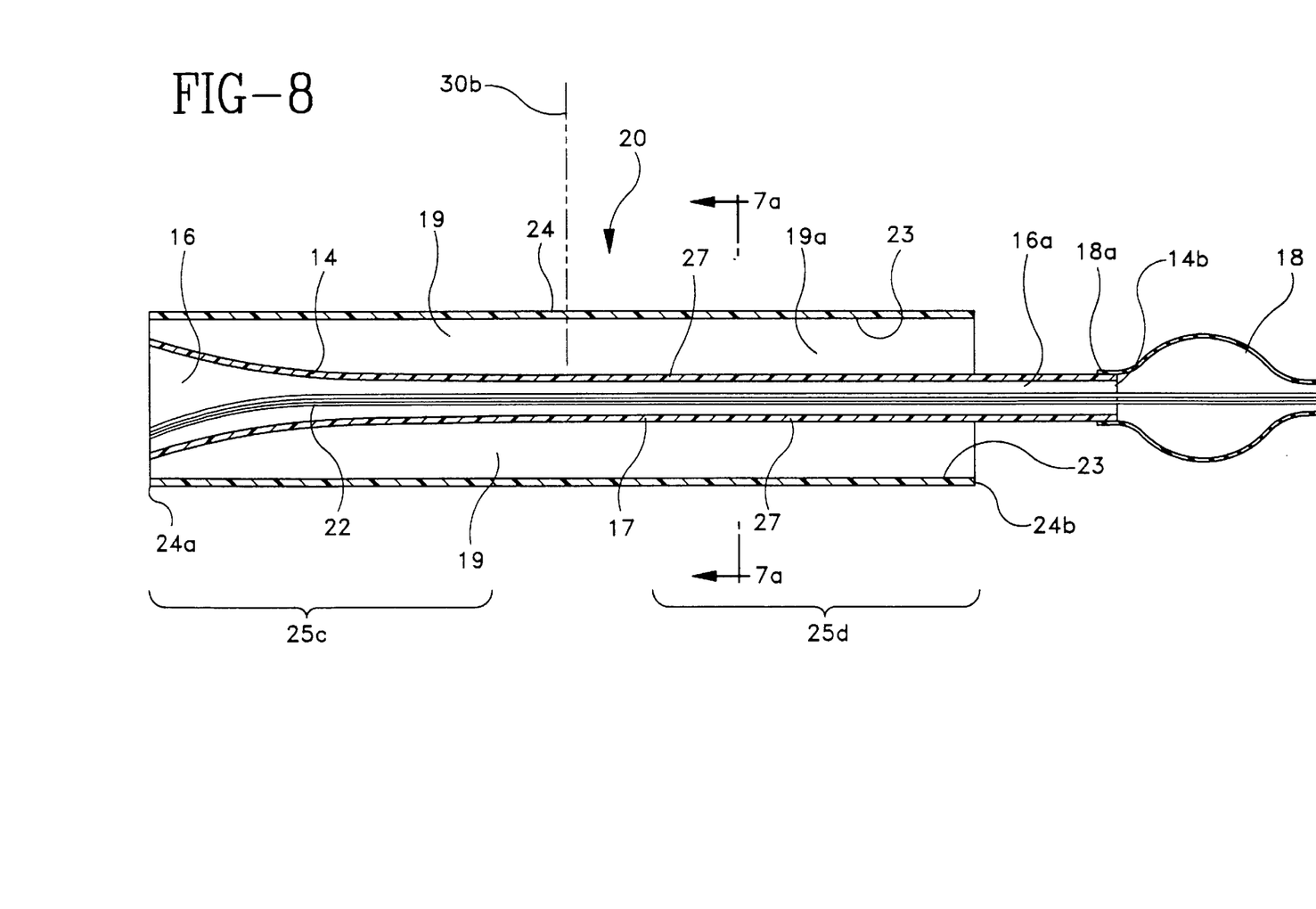
FIG. 8 is a sectional view of an embodiment of a balloon catheter and guide catheter assembly.

In another embodiment, the flow cross-sectional area in flow portion 16 may end decreasing nonlinearly between about 10% and about 60% of the longitudinal length measured from the proximal end 14a. Thereafter, the flow cross-sectional area in flow portion 16 may be constant, linear tapered, stepped or a combination of segments along the remaining longitudinal length. For example, a constant flow cross-sectional area 16a from 30a to 14b is shown in FIG. 6. Variants, including shorter or longer constant flow cross-sectional areas 16a are also possible. Also, the flow cross-sectional area in flow portion 19 in the balloon and guide catheter assembly 20 may end increasing nonlinearly between about 10% and about 60% of the longitudinal length measured from the proximal end 24a. Thereafter, the flow cross-sectional area may be constant, linear tapered, stepped or a combination of segments along the remaining coextensive axis. For example, a constant flow cross-sectional area 19a from 30b to 24b is shown in FIG. 8. Variants, including shorter or longer constant flow cross-sectional areas 19a are also possible.

In this application, the term "flow cross-sectional area" refers to any cross-sectional area formed in a balloon and guide catheter assembly where contrast media or the like will flow across; or any cross-sectional area formed in a catheter where fluid or the like will flow across. In this application, "flow portion 16" refers to a flow cross-sectional area that extends along at least a portion of a catheter longitudinal axis. In this application, "flow portion 19" refers to a flow cross-sectional area that extends along at least a portion of a balloon and guide catheter assembly longitudinal axis. In this application, the term "nonlinear" or "nonlinearly" refers to a rate of change in the flow cross-sectional area that is nonconstant or nonuniform per unit of change in the catheter or balloon and guide catheter assembly axial or longitudinal length. In this application, "proximal portion 15a" refers to the proximal most 40% of the elongated tube 14; "distal portion 15b" refers to the distal most 40% of the elongated tube 14; "proximal portion 25c"

refers to the proximal most 40% of the elongated tube 24; and "distal portion 25d" refers to the distal most 40% of the elongated tube 24.

The balloon catheter 10 and balloon and guide catheter assembly 20 may include over-the-wire, rapid-exchange, or other types of catheters and may be constructed of materials and by methods known in the art. The balloon catheter 10 and balloon and guide catheter assembly 20 may also include a guide wire lumen 22. Angioplasty catheters are disclosed for instance in U.S. Pat. Nos. 5,425,712 and 4,762,129. In addition, a diagnostic catheter is disclosed in U.S. Pat. No. 5,403,292. All documents cited herein are incorporated by reference in their entireties for all purposes.

The balloon catheter 10 has a distal end 14b that is connected to the proximal portion 18a of a balloon 18. The flow portion 16 communicates with and allows fluid to flow to and from the balloon 18. The connection of the proximal portion 18a of balloon 18 at the distal end 14b of the elongated tube 14 is preferably made by thermal, adhesive, laser bonding, or by conventional mechanical or chemical methods.

A typical balloon catheter 10 or balloon and guide catheter assembly 20 may have a syringe or hub assembly that is generally connected proximal to the proximal portions 15a, 25c which may be used to deflate the balloon 18 or to inject contrast media. For example, when a syringe plunger is drawn back, it first creates a vacuum in the syringe barrel and in the proximal portion 15a of flow portion 16. Balloon fluid, typically diluted contrast media, will first flow from the proximal portion 15a of flow portion 16 and thereafter fluid evacuation will continue distally and balloon 18 will deflate. During balloon 18 deflation, an amount of fluid flows from balloon 18, in a direction towards the proximal portion 15a of flow portion 16.

Generally, the flow rate through an inflation lumen or flow cross-sectional area is equal to the pressure divided by the flow resistance. In the present invention, the pressure is essentially constant which allows the fluid flow rate through the flow portion 16, 19 to be increased with a reduction in the flow resistance along the catheter or coextensive catheter longitudinal axis.

Generally, the flow resistance is proportional to the flow length divided by the flow cross-sectional area. In the present invention, the flow length is essentially constant. Therefore, when the flow cross-sectional area increases, the flow resistance generally decreases and the flow rate increases.

For example, an amount of fluid entering a lumen having a relatively constant flow cross-sectional area along the length of the lumen may experience generally constant resistance along the length of the lumen. In comparison, an amount of fluid entering a lumen having a nonlinear flow portion along the length of the lumen may experience progressively less flow resistance along the length of the lumen.

Figure 3:
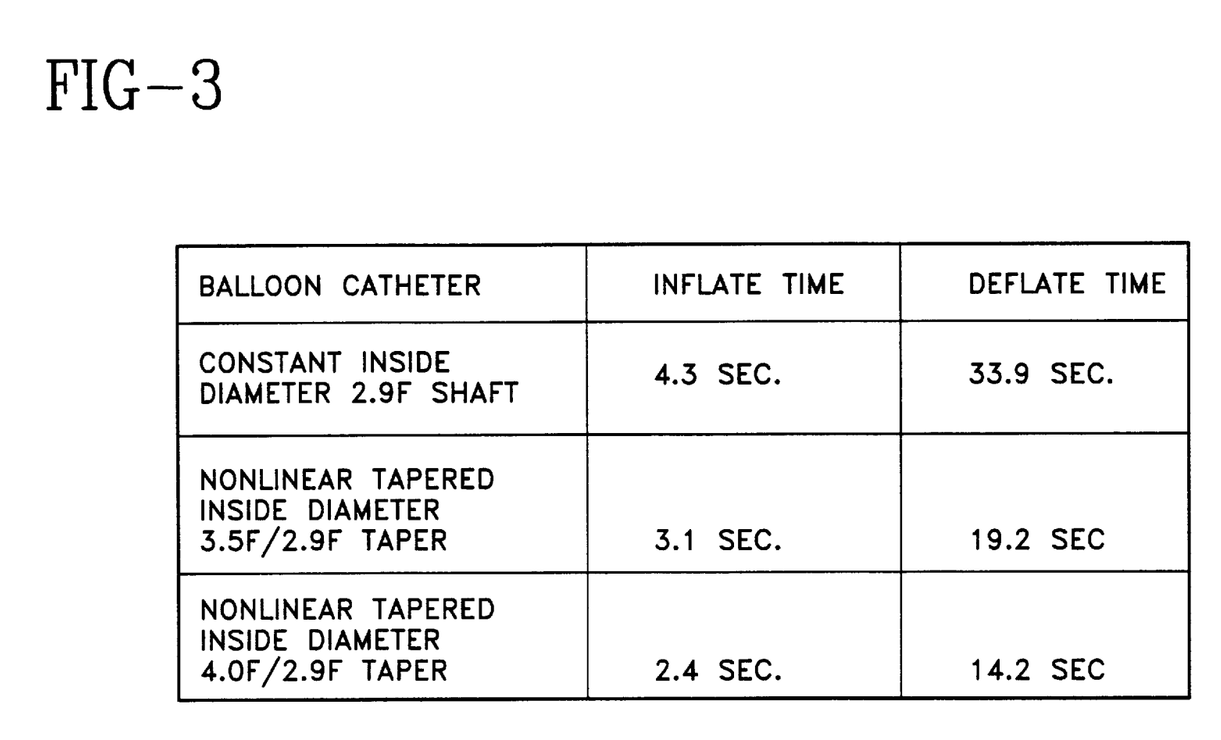
FIG. 3 is a table showing results of inflation and deflation testing in accordance with the invention, in connection with three different catheters.

Reference is made to FIG. 3 which illustrates the results of testing of a balloon catheter 10 incorporating a relatively nonlinear decreasing flow cross-sectional area in flow portion 16 from the proximal end 14a to the distal end 14b. The inflation and deflation times of the balloon 18 using a relatively nonlinear decreasing cross-sectional area from the proximal end 14a to the distal end 14b and having a larger proximal end 14a were faster than the inflation and deflation times of the balloon 18 measured using a relatively constant flow across-sectional area.

The nonlinear flow portion 16 in the balloon catheter 10 generally provides decreasing flow resistance in the proximal direction and the nonlinear flow portion 19 in the balloon and guide catheter assembly 20 generally provides decreasing flow resistance in the distal direction.

A preferred embodiment of the balloon and guide catheter assembly 20 has a first elongated tube 14 disposed in the second elongated tube 24. The balloon catheter 10 has proximal end 14a where fluid typically enters or exits the inflation lumen flow portion 16; and the balloon and guide catheter assembly 20 has a proximal end 24a where fluid enters or exits the flow portion 19 between the inside surface 23 of the second elongated tube 24 and the outside surface 27 of the first elongated tube 14. The first elongated tube 14 has at least one inflation lumen flow portion 16 extending from the proximal end 14a through to a distal end 14b connecting and communicating with a balloon 18.

In a preferred embodiment of the balloon and guide catheter assembly 20, the second elongated tube 24 has an inside and outside diameter that is substantially constant along its longitudinal length.

The nonlinear flow portion 19 in the balloon and guide catheter assembly 20 generally advantageously allows a relatively increased flow rate in the distal direction. Typically, fluid is forced under pressure by a syringe from the proximal portion 25c towards the distal portion 25d. Under pressure, the fluid enters the relatively small flow cross-sectional area in flow portion 19 at the proximal portion 25c. As the fluid or contrast media moves distally through the flow portion 19, the resistance generally progressively decreases as the flow cross-sectional area nonlinearly increases distally, resulting in an increased fluid flow rate.

In another embodiment of the balloon and guide catheter assembly 20, a nonlinear decreasing flow cross-sectional area in flow portion 19 from the proximal portion 25c to the distal portion 25d would provide a relatively greater fluid or blood flow rate of removal from a patient in the proximal direction.

The balloon and guide catheter assembly 20, first elongated tube 14 may have an outside diameter in the proximal portion 15a that nonlinearly decreases along the longitudinal axis to a smaller outside diameter at the distal portion 15b.

Figure 4:
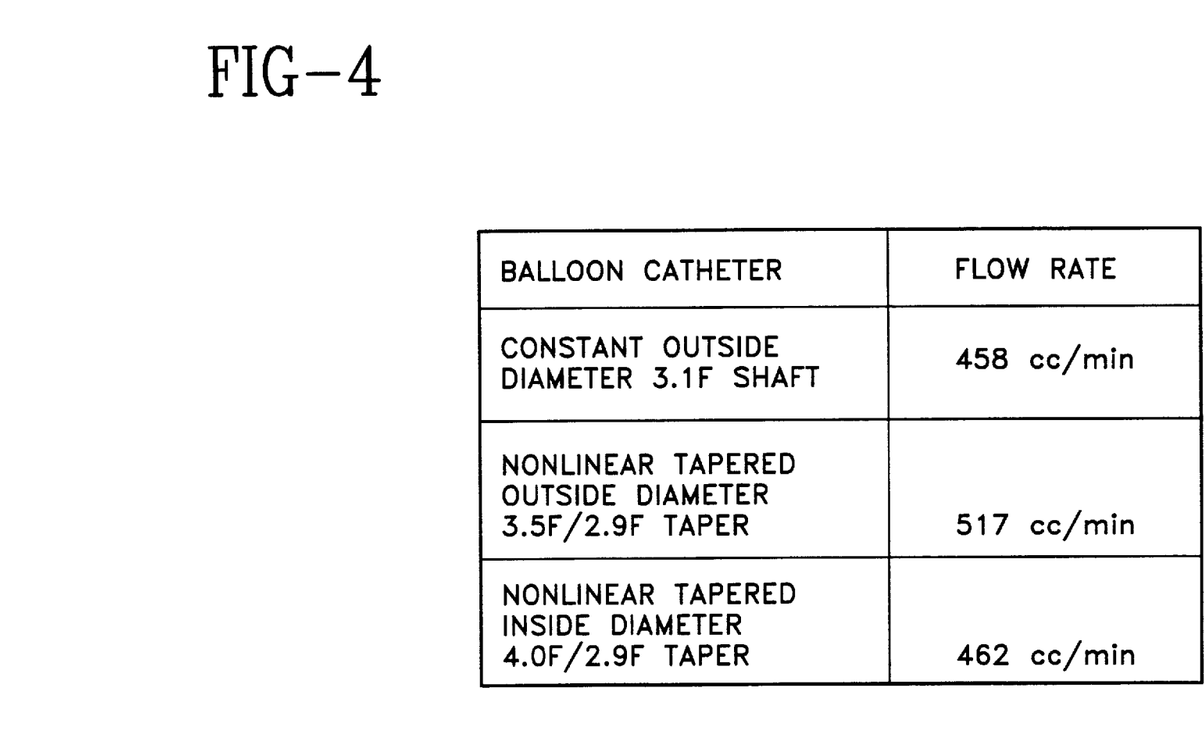
FIG. 4 is a table showing results of flow rate testing in accordance with the invention, in connection with three different catheters.

FIG. 4 illustrates the results of testing of a balloon and guide catheter assembly 20 incorporating a relatively nonlinear increasing flow portion 19 from the proximal end 24a to the distal end 24b.

The flow rate through the balloon and guide catheter assembly 20 using a nonlinear increasing flow portion 19 and using a balloon catheter 10 with a slightly larger proximal end 14a, a slightly smaller distal end 14b, a nonlinear decreasing flow portion 16; a wall 17 of substantial uniform thickness; and using an elongated tube 24 with a relatively constant inside diameter was relatively improved as compared to using a balloon and guide catheter assembly 20 having a relatively constant flow portion 19 along the coextensive catheter axis.

The flow rate through the balloon and guide catheter assembly 20 nonlinear increasing flow portion 19 using a balloon catheter 10 having a 4F proximal end 14a and 2.9F distal end 14b was relatively as good as the flow rate using a relatively constant 3.1F balloon catheter.

The flow rate through the balloon and guide catheter assembly 20 nonlinear increasing flow portion 19 using a balloon catheter 10 having a 3.5F proximal end 14a and 2.9F distal end was relatively improved as compared to the flow rate using a relatively constant 3.1F balloon catheter.

Figure 5:
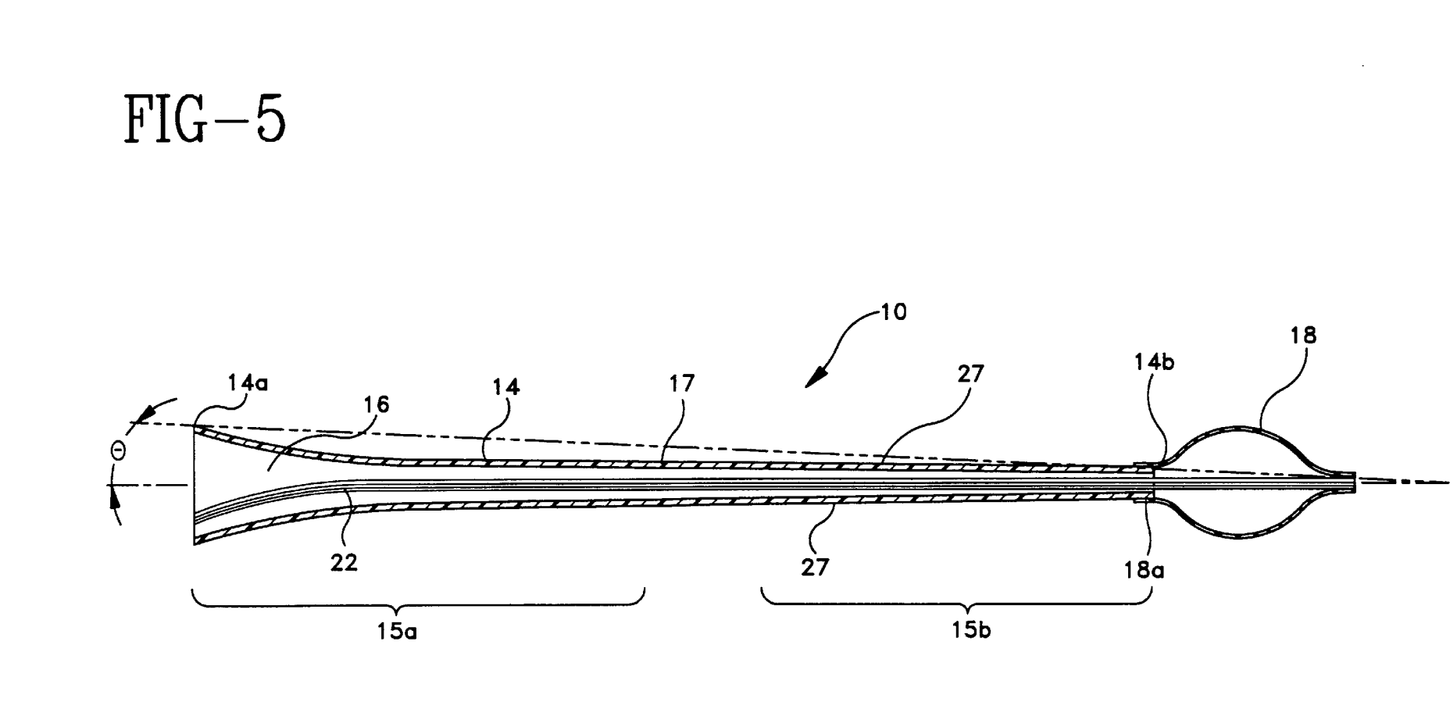
FIG. 5 is a view of FIG. 1 showing an imaginary line and angle.

The balloon catheter 10 and balloon and guide catheter assembly 20 each preferably have a wall 17 of substantial uniform thickness. In another embodiment, as illustrated in Fig.5 the balloon catheter 10 outside boundaries may be relatively defined by an angle formed by an imaginary line drawn between the proximal most nonlinear flow portion outside surface point of the proximal portion 15a and the distal most nonlinear flow portion outside surface point of the distal portion 15b with the balloon catheter 10 longitudinal axis of between about 1 degree and about 0.01 degree. In yet another embodiment, the balloon catheter 10 may have a constant outside diameter from the proximal portion 15a to the distal portion 15b. In another embodiment, the balloon catheter 10 may have at least 50% of the flow cross-sectional area decrease in flow portion 16 occurring within the first 25% of the longitudinal length. In yet another embodiment, the balloon and guide catheter assembly 20 may have a flow cross-sectional area in flow portion 19 that increases at least 20% distally along the longitudinal length measured from the proximal end 14a. In still another embodiment, the balloon catheter 10 may have a flow cross-sectional area in flow portion 16 that decreases at least 20% distally along the catheter longitudinal length measured from the proximal end 24a. In another embodiment, the balloon catheter 10 may have at least one flow portion 16 with a flow cross-sectional area that decreases nonlinearly distally along at least a portion of the longitudinal axis and thereafter has at least one additional substantially constant, linear tapered, or stepped flow cross-sectional area segment along the remaining longitudinal axis. In another embodiment, the balloon and guide catheter assembly 20 may be a kit having a balloon and guide catheter with nonlinear flow portions 16, 19 optimized for a particular performance.

The flow portions 16, 19 may be further engineered to provide a relatively higher or lower flow rate for a particular use. Also, in other embodiments of the balloon catheter 10, and balloon and guide catheter assembly 20, the wall thickness, flow cross-sectional areas, and flow portions 16, 19 may vary to meet mechanical and hydraulic objectives.

In other embodiments of the balloon catheter 10 and balloon and guide catheter assembly 20, additional nonlinear flow portions 16, 19 may be formed in the interior, exterior, or through ports of the elongated tubes 14, 24; and the flow cross-sectional area in nonlinear flow portions 16, 19 may vary along the longitudinal lengths of the first elongated tube 14 and second elongated tube 24, respectively. Multiple lumens having nonlinear flow portion 16 may be formed inside or along the exterior of the balloon catheter 10. Also, multiple nonlinear flow portions 16, 19 and lumen openings may be provided in a balloon and guide catheter assembly 20. Multiple lumens may be used in over-the-wire, rapid-exchange, and in a variety of catheters in a guide catheter.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. An intravascular catheter comprising an elongated tube having a proximal portion and a distal portion, an outside diameter, a balloon mounted on the distal portion of the elongated tube, and at least one lumen having a plurality of flow cross-sectional areas forming a longitudinal length and communicating with the balloon wherein the flow cross-sectional areas change in area at a nonuniform rate per unit of longitudinal length over at least a portion of the lumen;
wherein the flow cross-sectional area decreases at least 50% in area within about the first 25% of the lumen longitudinal length measured from the proximal end.

2. The intravascular catheter of claim 1 wherein the outside diameter of the elongated tube decreases in size at a nonlinear rate over at least a portion of the elongated tube.

3. The intravascular catheter of claim 2 wherein the elongated tube is at least partially inserted into a second elongated tube.

4. The intravascular catheter of claim 1 wherein the elongated tube further comprises a wall having a substantial uniform thickness.

5. The intravascular catheter of claim 1 wherein an angle formed by an imaginary line drawn between a proximal most nonlinear flow portion outside surface point and a distal most nonlinear flow portion outside surface point and the catheter longitudinal axis is between about 1 degree and about 0.01 degree.

6. The intravascular catheter of claim 1 wherein the outside diameter of the elongated tube at the proximal portion is greater than the outside diameter at the distal portion.

7. The intravascular catheter of claim 1 wherein the flow cross-sectional area decreases in area distally.

8. The intravascular catheter of claim 1 wherein the flow cross-sectional area ends decreasing in area between about 10% and about 60% of the lumen longitudinal length measured from the proximal end.

9. The intravascular catheter of claim 1 wherein the flow cross-sectional area decreases at least 20% in area distally along the longitudinal length of the elongated tube.

10. The intravascular catheter of claim 1 wherein the lumen has at least one portion that is substantially constant in area.

11. The intravascular catheter of claim 1 wherein the flow cross-sectional area has a shape selected from the group comprising circular, annular, oblong, irregular or a combination of shapes.

12. An intravascular catheter comprising an elongated tube having a proximal portion and a distal portion, an outside diameter, a balloon mounted on the distal portion of the elongated tube, and at least one lumen having a plurality of flow cross-sectional areas forming a longitudinal length and communicating with the balloon wherein the flow cross-sectional areas change in area at a nonuniform rate per unit of longitudinal length over at least a portion of the lumen;
wherein an angle formed by an imaginary line drawn between a proximal most nonlinear flow portion outside surface point and a distal most nonlinear flow portion outside surface point and the catheter longitudinal axis is between about 1 degree and about 0.01 degree.

13. The intravascular catheter of claim 12 wherein the flow cross-sectional area decreases at least 50% in area within about the first 25% of the lumen longitudinal length measured from the proximal end.

14. An intravascular catheter comprising an elongated tube having a proximal portion and a distal portion, an outside diameter, a balloon mounted on the distal portion of the elongated tube, and at least one lumen having a plurality of flow cross-sectional areas forming a longitudinal length and communicating with the balloon wherein the flow cross-sectional areas change in area at a nonuniform rate per unit of longitudinal length over at least a portion of the lumen;
wherein the flow cross-sectional area ends decreasing in area between about 10% and about 60% of the lumen longitudinal length measured from the proximal end.

15. An intravascular catheter comprising an elongated tube having a proximal portion and a distal portion, an outside diameter, a balloon mounted on the distal portion of the elongated tube, and at least one lumen having a plurality of flow cross-sectional areas forming a longitudinal length and communicating with the balloon wherein the flow cross-sectional areas change in area at a nonuniform rate per unit of longitudinal length over at least a portion of the lumen;

wherein the flow cross-sectional area decreases at least 20% in area distally along the longitudinal length of the elongated tube.

16. An intravascular catheter assembly comprising:

(a) a first elongated tube having at least one lumen with a plurality of first flow cross-sectional areas forming a longitudinal length, an outside diameter, a proximal end, a distal portion, a balloon mounted on the distal portion which communicates with the lumen, and an outside surface wherein the first flow cross-sectional areas change at a nonuniform rate per unit of axial length over at least a portion of the lumen;

(b) the outside diameter changing at a nonuniform rate per unit of longitudinal length over at least a portion of the first elongated tube; and (c) a second elongated tube having a longitudinal length, at least one lumen, and an inside surface;

wherein the first elongated tube is disposed at least partially in the second elongated tube lumen forming a plurality of second flow cross-sectional areas between the first elongated tube outside surface and the second elongated tube inside surface; and wherein the second flow cross-sectional area ends increasing in area between about 10% and about 60% of the longitudinal length of the catheter assembly measured from the proximal end.

17. The intravascular catheter assembly of claim 16 wherein the second flow cross-sectional areas increase in area at a nonuniform rate per unit of axial length distally.

18. The intravascular catheter assembly of claim 16 wherein the inside diameter of the second elongated tube is substantially constant.

19. The intravascular catheter assembly of claim 16 wherein the first flow cross-sectional area decreases in area distally in at least a portion of the lumen.

20. The intravascular catheter assembly of claim 16 wherein the second flow cross-sectional area increases in area distally in at least a portion of the catheter assembly.

21. The intravascular catheter assembly of claim 16 wherein at least one portion of the first or the second flow cross-sectional area is substantially constant in area.

22. The intravascular catheter assembly of claim 16 wherein the first or second flow cross-sectional area changes at a nonuniform or nonconstant rate per unit of change in longitudinal length.

23. An intravascular catheter assembly comprising:

(a) a first elongated tube having at least one lumen with a plurality of first flow cross-sectional areas forming a longitudinal length, an outside diameter, a proximal end, a distal portion, a balloon mounted on the distal portion which communicates with the lumen, and an outside surface wherein the first flow cross-sectional are areas change at a nonuniform rate nonuniform rate per unit of axial length over at least a portion of the lumen;

(b) the outside diameter changing at a nonuniform rate per unit of longitudinal length over at least a portion of the first elongated tube; and (c) a second elongated tube having a longitudinal length, at least one lumen, and an inside surface;

wherein the first elongated tube is disposed at least partially in the second elongated tube lumen forming a plurality of second flow cross-sectional areas between the first elongated tube outside surface and the second elongated tube inside surface; and wherein the second flow cross-sectional area increases at least 20% along the longitudinal length of the catheter assembly.

* * * * *